United States Patent [19]

Arena

[11] 4,401,823

[45] Aug. 30, 1983

[54] HYDROGENOLYSIS OF POLYHYDROXYLATED COMPOUNDS

[75] Inventor: Blaise J. Arena, Des Plaines, Ill.

[73] Assignee: UOP Inc., Des Plaines, Ill.

[21] Appl. No.: 260,865

[22] Filed: May 18, 1981

[51] Int. Cl.$^3$ .................. C07D 309/04; C07C 51/377
[52] U.S. Cl. .................................. 549/356; 549/427;
549/475; 562/515; 568/347; 568/350; 568/361;
568/698; 568/838; 568/861; 568/863; 568/876;
568/903; 585/638; 585/639; 585/733
[58] Field of Search ............... 568/903, 863, 861, 838,
568/347, 698, 350, 876, 361; 260/345.1, 345.9,
347.8; 562/515, 607; 585/733, 639, 638;
549/356, 427, 475

[56] References Cited

U.S. PATENT DOCUMENTS

| | | | |
|---|---|---|---|
| 1,963,997 | 6/1934 | Larchar | 568/903 |
| 1,963,999 | 6/1934 | Larchar | 568/863 |
| 4,090,978 | 5/1978 | Welsh et al. | 252/425.3 |
| 4,329,260 | 5/1982 | Lester et al. | 252/446 |

*Primary Examiner*—Nicky Chan
*Attorney, Agent, or Firm*—James R. Hoatson, Jr.; Raymond H. Nelson; William H. Page, II

[57] ABSTRACT

Polyhydroxylated compounds such as glucose, sucrose, sorbitol, etc. are subjected to a hydrogenolysis reaction at hydrogenolysis conditions which include a temperature in the range of from about 175° to about 250° C. and a pressure in the range of from about 10 to about 2000 pounds per square inch in the presence of a catalytic composition of matter. The catalyst comprises a carbonaceous pyropolymer possessing recurring units containing at least carbon and hydrogen atoms which is impregnated with a transition metal. The products which are obtained will include alcohols, acids, ketones, ethers, and hydrocarbons.

12 Claims, No Drawings

HYDROGENOLYSIS OF POLYHYDROXYLATED COMPOUNDS

Polyhydroxylated compounds which may be naturally occurring are available from a wide variety of renewable sources. Due to the ready availability of these compounds, it is possible to use the same for starting materials for obtaining useful chemical products. As an example of polyhydroxylated compounds, glucose, which is a naturally occurring 6-carbon sugar, may be treated in a catalytic reaction involving hydrogenation to form a 6-carbon atom polyol, namely sorbitol. The latter compound may then be subjected to a reaction such as hydrogenolysis in the presence of a reducing catalyst such as nickel composited on kieselguhr to form a lower polyol. Another reaction which sorbital may undergo is a dehydrocyclization reaction in the presence of a homogeneous metal salt catalyst such as nickel chloride, manganese chloride, lanthanum chloride, etc. to form hydroxy-substituted cyclic ethers.

However, it is also desirable to obtain other organic chemicals from such a polyol source, which chemicals have a wide variety of uses. It might be desirable to obtain hydrocarbons from the polyhydroxylated sources by removing all of the hydroxy radicals and, in the case of sorbitol, obtain n-hexane which may be used as an extract solvent for vegetable oils, as a component of fuels, etc. Other chemicals which may be obtained from such a polyhydroxylated source may include mono- or di-alcohols such as sec-butyl alcohol (2-butanol) which is used in the preparation of methylethyl ketone, as a solvent in varnishes, lacquers and paint removers, or in organic syntheses. Other mono-alcohols which may be obtained would include 2-pentanol and 3-pentanol which are used as solvents and in the preparation of pharmaceuticals. In addition, it is possible to obtain ketones and acids including acetic acid, which is a well-known article of commerce, propionic acid, butanoic acid, etc. However, the catalyst which is to be employed to obtain these particular types of compounds must be carefully selected. For example, it is not possible to utilize a catalyst in which alumina is present as a support in the event that a heterogeneous catalyst is to be employed inasmuch as alumina will react with the carbohydrate feed material. The oxy-aluminum compounds will react with the polyols to form an ether linkage between the aluminum and the polyol. The resulting complex will gel and it will then be impossible to remove the catalyst by filtration.

BRIEF SUMMARY OF THE INVENTION

This invention relates to a process for the hydrogenolysis of polyhydroxylated compounds. More specifically, the invention is concerned with a hydrolysis process whereby polyhydroxylated compounds may be subjected to treatment with a catalyst of the type hereinafter set forth in obtain desired chemical compounds.

It has now been discovered that by subjecting a polyhydroxylated compound which may be naturally occuring to a hydrogenolysis process in the presence of certain catalytic compounds, it is possible to obtain desired chemical compounds which will include hydrocarbons, acids, ketones, mono- and poly-hydroxylated compounds. The polyhydroxylated compounds which comprise the starting materials for the process of this invention, due to the fact that they are naturally occurring, are renewable, and thus can provide a constant source of supply. By converting the carbohydrates hereinafter described in greater detail to functionalized hydrocarbons, it is contemplated that they possess the potential to replace petroleum, which is non-renewable, as a source for many organic chemicals which are widely used in industry. This may be an important factor due to a possible instability regarding the availability of oil during the coming years as well as a possibility of increased cost thereof. The particular compositions of matter which are employed to effect the desired reaction will comprise a metal-impregnated carbonaceous pyropolymer in which the pyropolymer possesses recurring units containing at least carbon and hydrogen atoms.

It is therefore an object of this invention to provide a process for obtaining desired chemical compounds.

A further object of this invention is to provide a process where polyhydroxylated compounds are subjected to hydrogenolysis utilizing certain catalytic compositions of matter to provide the desired effect.

In one aspect, an embodiment of this invention resides in a process for the hydrogenolysis of a polyhydroxylated compound which comprises treating said compound at hydrogenolysis conditions in the presence of a catalyst comprising a metal-impregnated shaped carbonaceous pyropolymer possessing recurring units containing at least carbon and hydrogen atoms, and recovering the resultant products.

A specific embodiment of this invention is found in a process for the hydrogenolysis of sorbitol which comprises treating said sorbitol at a temperature in the range of from about 175° to about 250° C. and a pressure in the range of from about 10 to about 2000 pounds per square inch in the presence of a catalyst comprising a platinum-impregnated carbonaceous pyropolymer possessing recurring units containing at least carbon and hydrogen atoms, and recovering the desired product.

Other objects and embodiments will be found in the following further detailed description of the invention.

DETAILED DESCRIPTION OF THE INVENTION

As hereinbefore set forth, the present invention is concerned with a process for the hydrogenolysis of polyhydroxylated compounds. The process is effected by treating the compounds in the presence of a catalyst which comprises a metal-impregnated shaped carbonaceous pyropolymer possessing recurring units containing at least carbon and hydrogen atoms at hydrogenolysis conditions. The term "hydrogenolysis" as used in the present specification and appended claims is defined as the removal of at least one hydroxy-substituent from a polyhydroxylated compound. Examples of polyhydroxylated compounds which will undergo hydrogenolysis in the process of this invention will include monosaccharides such as glucose, fructose, galactose, mannose, xylose, erythrose, amino-monosaccharides such as glucoseamine, or galactoseamine, etc; disaccharides such as sucrose, lactose, maltose, isomaltose, etc; alditols such as sorbitol, mannitol, xylitol, galactitol, erythritol, etc; mono- and di-basic acids of saccharides such as gluconic acid, glucaric acid, etc; and soluble polysaccharides such as starch, etc. It is to be understood that the aforementioned compounds are only representative of the type of polyhydroxylated compounds which may undergo hydrogenolysis, and that the present invention is not necessarily limited thereto.

The aforementioned compounds will undergo hydrogenolysis in the presence of catalysts of the type hereinafter set forth in greater detail at hydrogenolysis conditions which will include an elevated temperature in the range of from about 175° to about 250° C., a temperature range of from about 190° to about 220° C. being preferred, and at an elevated pressure which may range from about 10 to about 2000 pounds per square inch. The particular pressure which is employed for the reaction may be afforded by the autogenous pressure of the hydrogen which is produced during the reaction, and which may be considered a reaction product, or, if a greater pressure is desired, the particular and predetermined operating pressure may be afforded by partial pressure of the hydrogen produced with the remainder of the desired pressure being provided for by the presence of an inert gas such as nitrogen, helium, argon, etc. in the reaction apparatus.

As hereinbefore set forth, the catalytic material which is employed to effect the hydrogenolysis of the present invention comprises a metal impregnated integral shaped replication of particle aggregates, said shapes including spheres, plates, pellets, rods, fibers, monoliths, powder, etc. The shaped catalyst which is impregnated with a metal will comprise a carbonaceous pyropolymer possessing recurring units containing at least carbon and hydrogen atoms. Examples of metals which are used to impregnate the carbonaceous pyropolymer will include transition metals such as chromium, molybdenum, tungsten, rhenium, manganese, copper, cadmium and the Group VIII metals of the Periodic Table including iron, cobalt, nickel, as well as the nobel metals such as platinum, palladium, rhodium, ruthenium, iridium and osmium. The aforesaid metals are impregnated on the surface of the carbonaceous pyropolymer in a manner hereinafter set forth in greater detail in an amount so that the metal loading of the finished catalyst will comprise from about 0.1 to about 25% by weight of the catalyst, and preferably in a range of from about 5 to about 15% by weight.

The integral shape replication support upon which the metal is impregnated may be prepared in any suitable manner. One method of preparing the support is to treat an inorganic support which possesses certain characteristics such as Apparent Bulk Density, surface area and pore structures with a pyropolymer precursor and thereafter pyropolymerizing said precursor by treatment at an elevated temperature which may range from about 400° to about 1200° C. to form the carbonaceous pyropolymer possessing recurring units containing at least carbon and hydrogen atoms on the surface of the inorganic support. The amount of carbonaceous pyropolymer which is deposited on the surface of the support will be sufficient to duplicate the physical shape and dimensions of the substrate material as well as a substantial portion of the pore structure thereof. For example, the inorganic support material which may act as a substrate may be characterized as having a surface area of from about 1 to about 500 m$^2$/g as well as a pore structure which includes both micropores and macropores. The pore structure of the resulting shaped replication will substantially duplicate the pore structures of the substrate material, this being especially true of the pore structures as to macropores which, for purposes of the catalyst of this invention, will refer to those pores which possess a pore size greater than 300 Å in diameter. Illustrative examples of inorganic supports will include refractory oxides such as alumina in various forms including gamma-alumina, eta-alumina, theta-alumina, or mixtures of inorganic refractory oxides such as zeolites, silica-alumina, silica-zirconia, zirconia-titania, zirconia-alumina, etc. As hereinbefore set forth, the shape of the inorganic support can be in any form desired, said particular form or shape of the substrate material being obtained by any method known in the art, such as manumerizing, pellettizing, nodulizing, etc.

In one method of preparing the composite, the inorganic support such as a refractory oxide is heated to a temperature of from about 400° to about 1200° C. in a reducing atmosphere containing an organic pyrolyzable compound. The organic pyropolymer precursors most commonly and preferably used for the purposes of this invention are members of the ground consisting of aliphatic hydrocarbons, aliphatic halogen derivatives, aliphatic oxygen derivatives, aliphatic sulfur derivatives, aliphatic nitrogen derivatives, organometallic compounds, alicyclic compounds, aromatic compounds, and heterocyclic compounds. Of the aliphatic hydrocarbons, the more common classes which may be utilized to perform this invention are alkanes, alkenes, alkynes, and alkadienes. Ethane, propane, butane and pentane are among the alkanes which may be successfully used in the performance of this invention. Similarly, alkenes which suffice include ethene, propene, 1-butene, 2-butene and 1-pentene. Alkynes which may be successfully used include ethyne, propyne, 1-butyne, 2-butyne, 1-pentyne, and 1-hexane. 1,3-Butadiene and isoprene are included among the alkadienes which may be utilized. Among the aliphatic halogen derivatives which suffice for the purposes of this invention, the monohaloalkane subgroup, chloromethane, bromoethane, 1-iodopropane, and 1-chlorobutane may be used. Polyhaloalkanes such as carbon tetrachloride, chloroform, 1,2-dichloroethane and 1,2-dichlorobutane may also be utilized. One unsaturated halo compound which may be utilized is chloroprene.

The aliphatic oxygen derivatives appropriate for use in this invention include the classes of alcohols, ethers, halohydrides and alkene oxides, saturated aldehydes and ketones, unsaturated aldehydes and ketones, ketenes, acids, esters, salts and carbohydrates. Various alcohols which may be utilized include ethanol, 2-butanol, 1-propanol, glycol, (e.g. 1,3-propanediol), and glycerol. Ethers utilized include ethyl ether and isopropyl ether. Appropriate halohydrins and alkene oxides include ethylene, chlorohydrin, propylene chlorohydrin, ethylene oxide, and propylene oxide. Suitable saturated aldehydes and ketones include formaldehyde, acetaldehyde, acetone, and ethyl methyl ketone. Unsaturated aldehydes and ketones which may be used include propenol, trans-2-butenal, and butenone. Ketene has also been successfully used as an organic pyrolyzable substance. Likewise, formic acid, acetic acid, oxalic acid, acrylic acid, chloroethanoic acid, formic anhydride and formyl chloride may also be utilized. Ethers such as methyl formate, ethyl formate and ethyl acetate may also be used. Salts such as sodium formate, potassium acetate and calcium propionate may be utilized as may a variety of carbohydrates. The broad classification of aliphatic sulfur derivatives may be broken down into the subclasses of alkanethiols, alkylthioalkanes, sulfonic acids, and alkyl sulfates and alkyl metallic sulfates. Suitable among the alkanethiols are ethyl mercaptan and n-propyl mercaptan. Among the alkylthioalkanes usable are the thioethers, alkyl sulfides, methyl sulfide, ethyl sulfide and methyl propyl sulfide.

Ethyl sulfonic acid and n-propyl sulfonic acid are sulfonic acids which may also be successfully used. Ethyl sulfate and sodium laurel sulfate are also appropriate for use.

The broad class of aliphatic nitrogen derivatives may be broken down into the subclasses of nitroalkanes, amides, amines, nitriles and carbylamines. Nitroethane and 1-nitropropane are exemplary of suitable nitroalkanes, while acetamide and propioamide are among the appropriate amides. Amines such as dimethylamine and ethylmethylamine, nitriles such as acetonitrile and propionitrile, and carbylamines such as ethyl isocyanide may also be used for the organic pyrolyzable substance of this invention. Organometallic compounds such as tetraisopropyl titanate, tetrabutyl titanate and 2-ethylhexyl titanate may also be used.

Particularly appropriate and preferred for use as the organo-pyrolyzable substance of this invention are the alicyclic compounds. Foremost among these are cyclohexane and cyclohexene. Aromatic compounds which include the subclasses of hydrocarbons, halogen compounds, oxygen derivatives, ethers, aldehydes, ketones, quinones, aromatic acids, aromatic sulfur derivatives, and aromatic nitrogen compounds may also be utilized. Among the many suitable hydrocarbons, benzene, naphthalene, anthracene, and toluene were successfully utilized. Benzyl chloride and benzal chloride are appropriate halogen compounds while phenol, o-cresol, benzyl alcohol and hydroquinone are among the suitable derivatives. Ethers such as anisole and phenetole and aldehydes, ketones, and quinones such as benzaldehyde, acetophenone, benzophenone, benzoquinone and anthraquinone may also be used. Aromatic acids such as benzoic acid, phenylacetic acid, and hydrocinnamic acid may be utilized while the aromatic sulfur derivative of benzene sulfonic acid will also serve successfully. The aromatic nitrogen compounds of nitrobenzene, 1-nitronaphthalene, aminobenzene and 2-aminetoluene may also be successfully used as the organic pyrolyzable substance of this invention. Among the heterocyclic compounds, five member ring compounds such as furan, proline, coumarone, thionaphthene, indole, indigo, and carbazole may be successfully utilized. Six member ring compounds such as pyran, coumarin and acridine may also be utilized.

As can be seen, an extremely wide latitude can be exercised in the selection of the organic pyrolyzable substance, since virtually any organic material that can be vaporized, decomposed and polymerized on the refractory oxide by heating will suffice. The resultant carbonaceous pyropolymer will possess recurring units containing at least carbon and hydrogen atoms; however, depending upon the pyropolymer precursor which has been selected, the pyropolymer may also contain other atoms such as nitrogen, oxygen, sulfur, or metals such as phosphorus etc.

In another embodiment, the composite may be prepared by impregnating the refractory inorganic oxide with a solution of a carbohydrate material such as dextrose, sucrose, fructose, starch, etc., and thereafter drying the impregnated support. After drying, the impregnated support is then subjected to pyrolysis temperatures in the range hereinbefore set forth whereby a carbonaceous pyropolymer similar in nature to those hereinbefore described is formed in at least a monolayer on the surface of the refractory inorganic oxide support.

Following this, the inorganic support is then chemically leached from the carbonaceous pyropolymer. The leaching is effected by treating said composite with either an acid or a base thereby forming a high surface area carbonaceous pyropolymer support which is a shaped replication of the original inorganic support. The leaching of the base material of the type hereinbefore set forth may be effected over a wide range of temperatures, said range being from about ambient (20°-25° C.) up to about 250° C. or more for a period of time which may range from less than 1 up to about 72 hours or more. It is to be understood that the operating parameters of the leaching step will vary over a wide range and will be dependent upon a combination of time, temperature, strength and the leaching solution, etc. Examples of acids or bases which may be utilized to leach out the base material, that is, the inorganic support such as a refractory inorganic oxide, will include inorganic acids such as phosphoric acid, sulfuric acid, nitric acid, hydrochloric acid, etc., organic acids such as methyl sulfonic acid, etc., strong bases such as sodium hydroxide, potassium hydroxide, lithium hydroxide, rubidium hydroxide, cesium hydroxide, etc. It is to be understood that the aforementioned leaching materials are only representative of the class of compounds which may be used and that any chemical which is capable of removing the refractory inorganic oxide while retaining the high surface area of the carbonaceous pyropolymer may be used.

The shaped replication of particle aggregates consisting of a carbonaceous pyropolymer containing recurring units of carbon and hydrogen atoms is then impregnated with an aqueous solution of a metal selected from the group consisting of chromium, molybdenum, tungsten, rhenium, manganese, copper, cadmium and the metals of Group VIII of the Periodic Table. The impregnation is effected by treating the carbonaceous pyropolymer structure with an aqueous or organic solution of the desired metal in an amount sufficient to deposit the metal on the surface of the support in an amount ranging from about 0.1 to about 25% by weight of the finished catalyst composite. The solution which is utilized to impregnate the carbonaceous pyropolymer structure is preferably aqueous in nature, some specific examples of these aqueous solutions being chloroplatinic acid, chloroplatinous acid, sodium platinate, potassium platinate, palladium chloride, chloropalladinic acid, sodium palladinate, potassium palladinate, palladium chloride, ruthenium chloride, rhodium chloride, rhodium nitrate, osmium chloride, iridium chloride, ferric bromide, ferric nitrate, ferrous iodide, ferrous perchlorate, nickel chloride, nickel nitrate, cobalt chloride, cobalt bromide, cobalt sulfate, chromium chloride, tungsten chloride, molybdenum chloride, copper chloride, cadmium chloride, cadmium acetate, cadmium sulfate, etc. It is to be understood that the aforementioned list of compounds are only representative of the type of salts or acids which may be employed to impregnate the metal on the surface of the carbonaceous pyropolymer structure, and that the present invention is not necessarily limited thereto.

After impregnation of the structure, usually at ambient temperature and pressure for a period of time sufficient to deposit the desired amount of metal on the surface of the structure, the solvent is removed by heating to a temperature in the range of from about 100° to about 400° C., the temperature being that which is sufficient to evaporate said solvent and leave the metal impregnated on the surface of the carbonaceous pyropolymer structure. Thereafter, the impregnated structure may then be dried at an elevated temperature ranging from about 100° to about 200° C. for a period of time which may range from about 2 to about 6 hours or more. Following this, the metal impregnated carbonaceous pyropolymer structure may then be subjected to a reducing step in the presence of a reducing atmosphere or medium such as hydrogen at elevated temperatures of from about 200° to about 600° C. for a period of time ranging from about 0.5 to 4 hours or more whereby the metallic compound is reduced to the metal in the form of particles.

In addition, if so desired, it is contemplated within the scope of this invention that an acidic compound may also be present in the reaction mixture. For example, inorganic acids such as phosphoric acid, sulfuric acid, nitric acid, hydrochloric acid, etc. or organic acids such as acetic acid, propionic acid, benzene sulfonic acid, toluene sulfonic acid, etc. may be added to the reaction mixture in an amount in the range of from about 0.01 to about 1% of the solution.

The process for the hydrogenolysis of the polyhydroxylated compounds may be effected in any suitable manner and may comprise either a batch or continuous type process. When a batch type operation is used, a quantity of the polyhydroxylated compound and the metal impregnated carbonaceous pyropolymer structure catalyst is placed in a reaction vessel which, in the preferred embodiment of the invention, comprises a pressure-resistant vessel. In addition, if so desired, the acidic compound may also be added following which the reaction vessel is sealed and purged with an inert gas such as nitrogen. Thereafter, the reactor may be pressurized by the addition of hydrogen or a combination of hydrogen and an inert gas of the type hereinbefore set forth until the desired operating pressure has been attained. The vessel is then heated to the predetermined temperature and maintained thereat for a period of time which may range from about 0.5 up to about 10 hours or more in duration. The desired operating pressure is maintained by venting, if so desired, any excess hydrogen which has been generated during the reaction. Upon completion of the desired residence time, heating is discontinued and, after the reaction vessel and contents have returned to room temperature, the excess pressure is vented. In the event that it is desired to shorten the cooling period, the reactor may be artificially cooled by internal cooling means such as coils. The reaction vessel is then opened and the reaction mixture is recovered. The liquid portion of the reaction mixture is separated from the catalyst by conventional means such as decantation, filtration, centrifugation, etc. and thereafter, the various components of the mixture including acids, ketones, lower polyols, hydrocarbons, etc. are separated and recovered by fractional distillation, crystallization, etc.

It is also contemplated within the scope of this invention that the hydrogenolysis of polyhydroxylated compounds may be effected in a continuous manner of operation. When such a type of operation is employed, the polyhydroxylated compound is continuously charged to a reaction vessel containing the metal-impregnated carbonaceous pyropolymer structure catalyst, said reaction vessel being maintained at the proper operating conditions of temperature and pressure. After passage through the vessel for a predetermined period of time, the reaction mixture is continuously withdrawn and subjected to conventional means of separation similar in nature to those hereinbefore set forth, any unreacted starting material being recycled to the reaction vessel as a portion of the feedstock, while the reaction products are separated and recovered. Inasmuch as the catalyst which is employed for this reaction is solid in nature, it is possible to employ various types of continuous processes to effect the desired reaction. For example, the catalyst may be positioned in the reaction vessel as a fixed bed, while the polyhydroxylated feedstock is passed over said bed in either an upward or downward flow. Another type of continuous process which may be employed comprises the moving bed type in which the catalyst and the feedstock are passed through said reaction vessel either concurrently or countercurrently to each other. Alternately, a slurry type process may be used in which the catalyst is carried into the reaction vessel as a slurry in the feedstock and is continuously withdrawn along with the reaction products.

The following examples are given for purposes of illustrating the process for the hydrogenolysis of polyhydroxylated compounds. However, it is to be understood that these examples are given merely for purposes of illustration and that the present process is not necessarily limited thereto.

EXAMPLE I

A catalyst for use in the hydrogenolysis of polyhydroxylated compounds was prepared by calcining ⅛" diameter alumina spheres at a temperature of 482° C. for a period of 2 hours. Following this, the spheres were placed in an inert atmosphere and a carbonaceous pyropolymer layer was deposited on these spheres by pyrolyzing hexane in the presence of said spheres at a temperature of 788° C. in an inert atmosphere. The resulting composite layer was then leached by immersion in a 96% phosphoric solution at a temperature of 160° C. for a period of 24 hours. The resulting shaped replication of particle aggregates comprising a carbonaceous pyropolymer structure possessing recurring units of carbon and hydrogen atoms was then impregnated by immersion in an aqueous chloroplatinic acid solution for a period of 1 hour. Thereafter, the impregnated composite was dried and calcined at a temperature of 250° C. for a period of 2 hours. The desired catalytic composite which was prepared according to this method contained 15% platinum by weight.

To effect the hydrogenolysis, 2 grams of the catalyst prepared according to the above paragraph along with 150 ml of a 33% aqueous sorbitol solution was placed in a 300 cc stainless steel stirred autoclave equipped with internal cooling coils at a constant pressure hydrogen delivery system. After placing the said solution and the catalyst in the reaction vessel, it was then sealed and charged with nitrogen. The reactor was then pressurized to an initial operating pressure of 700 psi with hydrogen, and the vessel was heated to a temperature of 225° C. After the vessel had reached the desired temperature, excess hydrogen pressure which was generated by the thermal expansion was vented and the pressure was maintained at 700 psi for the duration of the reaction time. After a period of 5.5 hours had passed, heating was discontinued and the reactor was cooled by utilizing the internal cooling coils. Upon reaching room temperature which took a period of 0.75 hours the excess pressure was vented and the reaction mixture was recovered. The solution was decanted from the catalyst and subjected to analysis. The product solution had a strong ultra-violet absorbency and, in addition, it was found that there had been a 99% conversion of the sorbitol. A qualitative analysis of the product utilizing infra-red, gas chromatography and gas chromatography-mass spectrometry methods disclosed that the solution contained ketones such as acetone, 2-butanone, 2-pentanone, 2-hexanone, 3-hexanone, cyclopentanone, 2-methylcyclopentanone, 3-methylcyclopentanone, 3-hydroxy-2-butanone, 2,5-hexanedione; alcohols including 2-butanol, 2-pentanol, 3-pentanol, 2-hexanol, 3-hexanol, cyclopentanol, 2-methylcyclopentanol; cyclic ethers such as 2-methyltetrahydropyran, hydroxytetrahydrofuran, 2-methanoltetrahydropyran; carboxylic acids such as acetic acid, propionic acid, butanoic and hydrocarbons such as methane, ethane, propane, propylene as well as hydrogen.

EXAMPLE II

In a manner similar to that set forth in Example I above, a catalyst comprising 30% nickel composited on a carbonaceous pyropolymer structure was prepared. Again, 2 grams of this catalyst were placed in a stainless steel autoclave along with 150 ml of a 33% aqueous sorbitol solution. The reaction vessel was sealed, charged with nitrogen and pressured to 700 psi with hydrogen. The autoclave was then heated to a temperature of 225° C. during a heat-up period of 1 hour. At the end of the 1 hour period, the excess hydrogen pressure was vented and the pressure was maintained at 700 psi during an operating time of 5.5 hours. At the end of the reaction time, heating was discontinued and the reactor was cooled using internal cooling coils for a period of 45 minutes. Upon reaching room temperature, the hydrogen pressure was vented, the autoclave was opened and the reaction mixture was recovered therefrom. The solution was decanted from the catalyst and analyzed. It was found that there had been a 93% conversion of the sorbitol with less than 1% yield of polyols, the remainder of the products comprising a mixture of ketones, alcohols, acids, ethers, and hydrocarbons.

EXAMPLE III

To illustrate the necessity for the presence of a catalyst of the type hereinbefore set forth, that is, a metal-impregnated carbonaceous pyropolymer structure possessing recurring units containing at least carbon and hydrogen atoms, a series of experiments were performed in which the sorbitol was subjected to hydrogenolysis in a manner similar to that hereinbefore set forth. In one experiment, the catalyst comprised 5 grams of nickel composited on kieselguhr. The process resulted in only a 37% conversion of the sorbitol with a 16.5% yield of polyols such as ethylene glycol, glycerol, 1,2-propanediol, etc. Any gases produced were produced during the reaction and the product solution did not disclose any ultra-violet absorption, this indicating the absence of any carbonyl compounds.

Another experiment was performed in which sorbitol was treated with a catalyst comprising 5% platinum composited on carbon, the reaction conditions being similar to those described in Examples I and II above. The results of this experiment showed that there had been a 16% conversion of the sorbitol along with a 7.5% yield of polyols and again, no ultra-violet absorbents.

When the experiment was repeated by treating an aqueous sorbitol solution in the presence of a catalyst comprising only the carbonaceous pyropolymer structure under identical operating conditions of pressure and time, the product, upon analysis, disclosed only an 18% conversion of the sorbitol with less than a 1% polyol yield and no ultra-violet absorption.

EXAMPLE IV

In this example, a hydrogenolysis process was run in which 150 ml of a 33% aqueous sorbitol solution was placed in a 300 cc stainless steel stirred autoclave equipped with internal cooling coils along with 2 grams of a catalyst comprising 15% by weight of platinum impregnated on a carbonaceous pyropolymer structure possessing recurring units containing at least carbon and hydrogen atoms. The reaction vessel was sealed and purged at atmospheric pressure. Following this, the autoclave was heated to a temperature of 225° C. and maintained thereat for a period of 5.5 hours while maintaining a pressure of 300 psi. Upon completion of the desired reaction time, heating was discontinued and, after the autoclave had returned to room temperature using internal cooling coils, the excess pressure was vented. The autoclave was opened and the reaction mixture recovered therefrom. The solution was separated from the catalyst and subjected to analysis, said analysis disclosing that there had been an 80% conversion of the sorbitol along with a production of carboxylic acids, aliphatic ketones, as well as hydrocarbons.

EXAMPLE V

In a manner similar to that hereinbefore set forth, other polyhydroxylated compounds such as mannitol, glucose, lactose, and sucrose may be subjected to a hydrogenolysis process by treatment at a temperature of about 200° C. and a hydrogen pressure of about 700 psi in the presence of various catalysts such as palladium composited on a carbonaceous pyropolymer structure, rhenium composited on a carbonaceous pyropolymer structure and copper composited on a carbonaceous pyropolymer structure, to produce dehydroxylated products such as ketones, ethers, alcohols, acids and hydrocarbons.

I claim as my invention:

1. A process for the hydrogenolysis of a polyhydroxylated compound selected from the group consisting of monosaccharides, disaccharides, mono-basic acids of saccharides, dibasic acids of saccharides, amino-monosaccharides, and alditols which comprises treating said compound at hydrogenolysis conditions in the presence of a catalyst comprising a shaped carbonaceous pyropolymer possessing recurring units containing at least carbon and hydrogen atoms impregnated with a metal selected from the group consisting of chromium, molybdenum, tungsten, rhenium, manganese, copper, cadmium and a Group VIII metal, and recovering the resultant mono-alcohol, hydrocarbon, ether, ketone and carboxylic acid products, wherein said reaction products are of a different class of compounds than the compounds that undergo hydrogenolysis.

2. The process as set forth in claim 1 in which said hydrogenolysis conditions include a temperature in the range of from about 175° to about 250° C. and a pressure in the range of from about 10 to about 2000 pounds per square inch.

3. The process as set forth in claim 1 in which said metal is present in said catalyst in an amount in the range of from about 0.1 to about 25% by weight of said catalyst.

4. The process as set forth in claim 3 in which said metal is platinum.

5. The process as set forth in claim 3 in which said metal is palladium.

6. The process as set forth in claim 3 in which said metal is rhenium.

7. The process as set forth in claim 3 in which said metal is copper.

8. The process as set forth in claim 1 in which said alditol is sorbitol.

9. The process as set forth in claim 1 in which said alditol is mannitol.

10. The process as set forth in claim 1 in which said monosaccharide is glucose.

11. The process as set forth in claim 1 in which said disaccharide is lactose.

12. The process as set forth in claim 1 in which said disaccharide is sucrose.

* * * * *